(12) United States Patent　(10) Patent No.: US 6,905,493 B2
Lentz　(45) Date of Patent: Jun. 14, 2005

(54) MECHANICALLY EXTENDED SPIRAL CRYOTIP FOR A CRYOABLATION CATHETER

(75) Inventor: David J. Lentz, La Jolla, CA (US)

(73) Assignee: CryoCor, Inc., San Diego, CA (US)

( * ) Notice: Subject to any disclaimer, the term of this patent is extended or adjusted under 35 U.S.C. 154(b) by 74 days.

(21) Appl. No.: 10/405,131

(22) Filed: Apr. 1, 2003

(65) Prior Publication Data

US 2004/0199153 A1 Oct. 7, 2004

(51) Int. Cl.[7] ............................................. A61B 18/04
(52) U.S. Cl. ...................................... 606/21; 606/23
(58) Field of Search .......................... 606/20, 21, 23, 606/41

(56) References Cited

U.S. PATENT DOCUMENTS

| 5,322,508 | A | 6/1994 | Viera |
| 5,833,685 | A | 11/1998 | Tortal et al. |
| 6,237,355 | B1 | 5/2001 | Li |
| 6,245,064 | B1 | 6/2001 | Lesh et al. |

| 2002/0111618 | A1 | * | 8/2002 | Stewart et al. ................ 606/41 |
| 2004/0167509 | A1 | * | 8/2004 | Taimisto ....................... 606/41 |

FOREIGN PATENT DOCUMENTS

WO　WO 02/07625 A2　1/2002

* cited by examiner

Primary Examiner—Lee S. Cohen
(74) Attorney, Agent, or Firm—Nydegger & Associates

(57) ABSTRACT

A system and method for cryoablating tissue at a target site in a patient includes a cryotip attached to the distal end of a catheter tube. The cryotip is made of a conductive polymer material that is heat set into a spiral configuration. Inside the cryotip is a configuration lumen. The cryotip assumes a straight configuration when a straightening member is positioned in the configuration lumen, and it assumes the spiral configuration when the straightening member is absent from the configuration lumen. The cryotip in the straight configuration is guided through the vasculature of a patient to the target site. At the target site, the straightening member is removed to configure the cryotip into the spiral configuration to contact the cryotip with circumferential tissue around the target site. A refrigerant fluid is then introduced into the expansion chamber of the cryotip to cool the tip to cryoablate the circumferential tissue.

17 Claims, 2 Drawing Sheets

MECHANICALLY EXTENDED SPIRAL CRYOTIP FOR A CRYOABLATION CATHETER

FIELD OF THE INVENTION

The present invention pertains generally to devices and methods for cryoablating tissue in the vasculature of a patient. More particularly, the present invention pertains to devices and methods of cryoablating peripheral tissue around a circumferential opening in the vasculature of a patient. The present invention is particularly, but not exclusively, useful for cryoablating peripheral tissue around the ostium of a patient's pulmonary vein to treat atrial fibrillation.

BACKGROUND OF THE INVENTION

Atrial fibrillation is the most common form of heart arrhythmia. In a normally functioning heart, an electrical system directs electrical impulses through the heart in an organized fashion to stimulate the heart so that it properly contracts. Specifically, the upper chambers (atria) and the lower chambers (ventricles) of the heart are stimulated to contract in a synchronous manner. Fundamentally, atrial fibrillation is the loss of synchronicity between the upper chambers and the lower chambers of the heart. In effect, atrial fibrillation is a very fast, uncontrolled heart rhythm in which the atria quiver instead of beating. Atrial fibrillation can be described as a storm of electrical energy that travels across both atria causing them to fibrillate at 300 to 600 times a minute. This storm of electrical energy interferes with the electrical system of the heart and prevents the heart from functioning properly.

Research has shown that almost all atrial fibrillation occurs at the ostium of the pulmonary veins at the left ventricle of the heart. Specifically, atrial fibrillation is the result of abnormal electrical signals that pass through the pulmonary vein openings and enter the heart. Inside the heart, these abnormal electrical signals can disrupt the electrical system and cause the heart to beat abnormally. Accordingly, preventing the abnormal electrical signals from reaching the heart is one method for treating atrial fibrillation. In one such treatment method, the ostium of the pulmonary veins are circumferentially ablated to destroy tissue around the periphery of the ostium. Consequently, the destroyed tissue is no longer able to initiate or conduct any type of electrical signal. Accordingly, abnormal electrical signals are prevented from reaching the heart through the pulmonary veins.

One technique for ablating the tissue around the ostium of the pulmonary veins involves cryoablating the tissue with a cryoablation catheter. In this technique, the cryotip of the cryoablation catheter is repeatedly contacted with tissue around the periphery of the ostium to cryoablate the tissue in a piecemeal fashion. Ideally, the cryoablated tissue is destroyed to form a uniform and continuous circumferential lesion around the periphery of the ostium. If properly formed, the lesion will not conduct electrical signals that may cause atrial fibrillation. In some instances, however, this procedure may result in a non-uniform or discontinuous circumferential lesion that does not adequately block the abnormal electrical signals. This occurs because it is difficult to form a uniform and continuous circumferential lesion with successive cryoablations that are performed in a piecemeal fashion. Specifically, the cryotip of the catheter must be repeatedly and accurately positioned around the periphery of the ostium to properly form the circumferential lesion. Moreover, this procedure is time consuming because it requires extensive manipulation of the cryotip around the ostium.

In light of the above, it is an object of the present invention to provide a device and method for performing single-step cryoablation of circumferential tissue in the vasculature of a patient. Another object of the present invention is to provide a device and method for cryoablating peripheral tissue around the ostium of a pulmonary vein to treat atrial fibrillation. Still another objection of the present invention is to provide a device and method for cryoablating circumferential tissue in the vasculature of a patient in an efficient and reliable manner.

SUMMARY OF THE INVENTION

The present invention provides a cryoablation catheter that is capable of cryoablating peripheral tissue around a target site in the vasculature of a patient. In detail, the cryoablation catheter includes a catheter tube, a cryotip, and a straightening member. The cryotip includes a reconfiguration segment that has a proximal end attached to the distal end of the catheter tube, and a tip portion that is attached to the distal end of the reconfiguration segment. Importantly, the reconfiguration segment is configurable to assume either a straight configuration or a spiral configuration. More specifically, the reconfiguration segment includes a configuration lumen that is dimensioned to receive the straightening member. When the straightening member is positioned in the configuration lumen, the reconfiguration segment assumes the straight configuration. When the straightening member is absent from the configuration lumen, the reconfiguration segment assumes the spiral configuration. In the spiral configuration, the reconfiguration segment forms a spiral (coil) with a sufficiently large diameter to establish contact with the peripheral tissue that is to be cryoablated. Cryoablation of the peripheral tissue can then be accomplished in a single-step operation.

In detail, the catheter tube is formed with a fluid lumen, a return lumen, and a configuration lumen that extend between its proximal and distal ends. The reconfiguration segment is also formed with a fluid lumen and a return lumen that extend between its proximal and distal ends. Unlike the catheter tube, however, the configuration lumen of the reconfiguration segment extends from its proximal end toward its distal end, but does not extend all the way to the distal end. Structurally, the proximal end of the reconfiguration segment is affixed in a fluid-tight seal to the distal end of the catheter tube. Accordingly, the three lumens of the catheter tube are respectively connected to the corresponding three lumens of the reconfiguration segment.

Importantly, the reconfiguration segment is made of a thermally conductive polymer and is preformed into a desired shape. Preferably, the reconfiguration segment is made of a thermally conductive polymer that is heat set into the spiral configuration. Accordingly, in this case, the reconfiguration segment is preformed into a spiral or coiled shape.

The tip portion of the cryotip surrounds an expansion chamber and preferably has a cylindrical shape. Additionally, the tip portion has an open proximal end that provides fluid access to the expansion chamber and an opposing closed distal end that partially encloses the expansion chamber. Structurally, the proximal end of the tip portion is attached to the distal end of the reconfiguration segment in a fluid-tight seal. Furthermore, the fluid lumen of the reconfiguration segment extends past its distal end and into the expansion chamber of the tip portion. Accordingly, the expansion chamber is in fluid communication with the fluid lumen of the reconfiguration segment. For the present invention, the expansion chamber is also in fluid communication with the return lumen of the reconfiguration segment.

The present invention further includes a supply line and a fluid source. In detail, the proximal end of the supply line is connected to a fluid supply, and the distal end of the supply line is connected to the fluid lumen at the proximal end of the catheter tube. Accordingly, the fluid lumen of the catheter tube is in fluid communication with the fluid supply. Consequently, the expansion chamber of the tip portion is in fluid communication with the fluid source through the supply line and the fluid lumens of the reconfiguration segment and catheter tube.

The straightening member of the present invention is preferably a thin, elongated, stiff rod with a circular cross-section. Structurally, the straightening member is more rigid than the reconfiguration segment of the cryotip so that the reconfiguration segment conforms to the shape of the straightening member when the latter is inserted into the configuration lumen of the reconfiguration segment. Furthermore, the straightening member can be either inserted or withdrawn from the configuration lumens. It is important, however, that when it is inserted into the configuration lumen, the straightening member has the required flexibility to be advanced through the vasculature of a patient.

In operation, the straightening member is inserted through the configuration lumen of the catheter tube and into the configuration lumen of the reconfiguration segment. This places the reconfiguration segment into the straight configuration. In the straight configuration, the reconfiguration segment is advanced through the vasculature of a patient to a target site. At the target site, the straightening member is withdrawn from the configuration lumen of the reconfiguration segment. This places the reconfiguration segment into the spiral configuration. In the spiral configuration, the reconfiguration segment is urged into contact with peripheral tissue at the target site.

A refrigerant fluid (e.g. Nitrous Oxide) is supplied by the fluid source and introduced into the expansion chamber of the tip portion. The refrigerant fluid expands in the expansion chamber to cool the tip portion. This also cools the reconfiguration segment which, as mentioned above, is made of a thermally conductive polymer. Consequently, the peripheral tissue that is in contact with the reconfiguration segment can be cryoablated in a single-step operation.

For withdrawal of the cryocatheter from the vasculature of the patient, the straightening member can be reinserted into the configuration lumen of the reconfiguration segment to configure it into the straight configuration.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
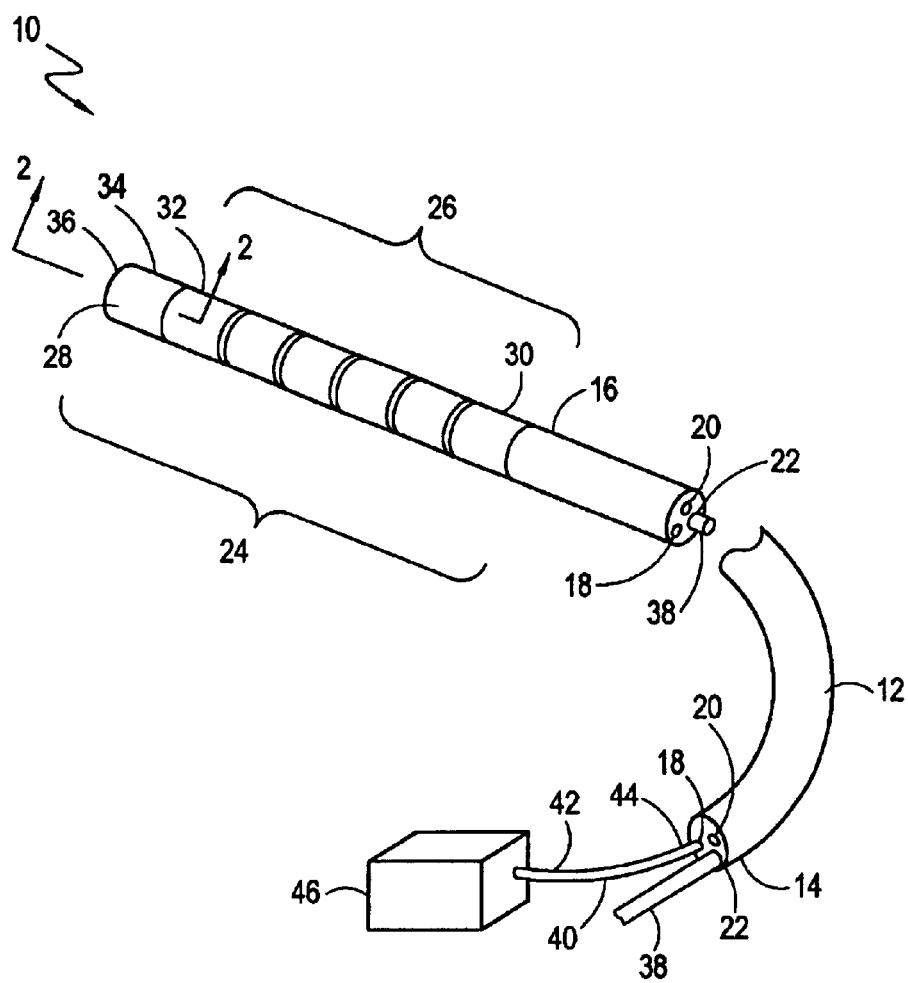
FIG. 1 is a perspective view of a cryoablation catheter in accordance with the present invention, with peripheral components of the system shown schematically.

Referring initially to FIG. 1, a cryoablation catheter system in accordance with the present invention is shown and is generally designated 10. The system 10 includes a catheter tube 12 that has a proximal end 14 and a distal end 16. The catheter tube 12 is formed with a fluid lumen 18, a return lumen 20 and a configuration lumen 22, each extending between the proximal end 14 and the distal end 16 of the catheter tube 12. Additionally, the system 10 includes a cryotip 24 that has a reconfiguration segment 26 and a tip portion 28. The reconfiguration segment 26 has a proximal end 30 and a distal end 32. As shown, the proximal end 30 of the reconfiguration segment 26 is attached to the distal end 16 of the catheter tube 12. The tip portion 28 has an open proximal end 34 and a closed distal end 36. The proximal end 34 of the tip portion 28 is attached to the distal end 32 of the reconfiguration segment 26. The system 10 also includes a straightening member 38. As shown, the straightening member 38 is positioned in the configuration lumen 22 of the catheter tube 12. Furthermore, the system 10 includes a supply line 40 that has a proximal end 42 and a distal end 44. The proximal end 42 of the supply line 40 is connected to a fluid source 46, and the distal end 44 of the supply line 40 is connected to the fluid lumen 18 of the catheter tube 12. Preferably, the supply line 40 has a hollow, tubular shape.

Figure 2:
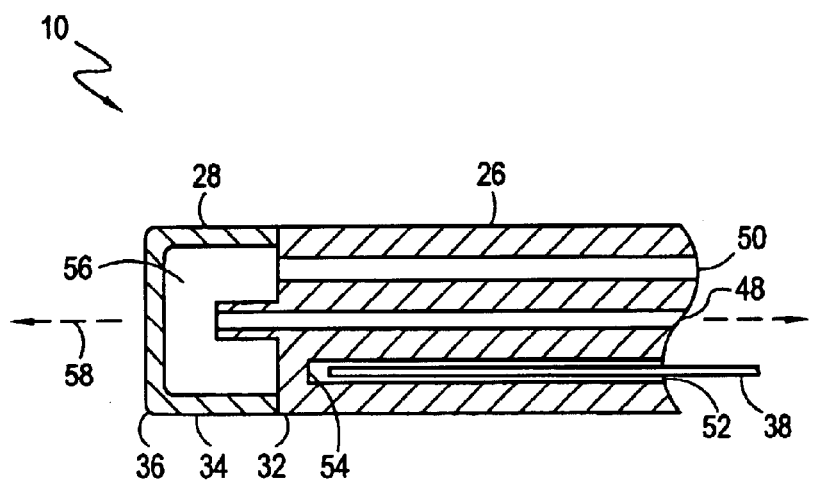
FIG. 2 is a cross-sectional view of the cryotip of the cryoablation catheter as seen along the line 2—2 in FIG. 1.

Referring now to FIG. 2, it can be seen that the reconfiguration segment 26 is formed with a fluid lumen 48, a return lumen 50 and a configuration lumen 52. As envisioned for the present invention, the fluid lumen 48 and the return lumen 50 each extend between the proximal end 30 (FIG. 1) and the distal end 32 of the reconfiguration segment 26. As further envisioned for the present invention, the configuration lumen 52 extends from the proximal end 30 of the reconfiguration segment 26 substantially to the distal end 32 of the reconfiguration segment 26, but it does not extend all the way to the distal end 32. Instead, the configuration lumen 52 has a closed end 54 at the distal end 32 of the reconfiguration segment 26 that prevents the straightening member 38 from being inserted completely through the reconfiguration segment 26. Importantly, the reconfiguration segment 26 is made of a flexible material that can be preformed into a desired shape. Also, the reconfiguration segment 26 is preferably made of a thermally conductive polymer material that can be heat set into a spiral (coil) shape to preform the reconfiguration segment 26 into a spiral configuration (See FIG. 4).

Structurally, the lumens 48, 50 and 52 of the reconfiguration segment 26 are respectively connected to the corresponding lumens 18, 20 and 22 of the catheter tube 12 (FIG. 1). Furthermore, the proximal end 30 of the reconfiguration segment 26 is affixed in a fluid-tight seal to the distal end 16 of the catheter tube 12. Accordingly, the fluid lumen 48 of the reconfiguration lumen 26 is in fluid communication with the fluid lumen 18 of the catheter tube 12, and the return lumen 50 of the reconfiguration segment 26 is in fluid communication with the return lumen 20 of the catheter tube 12.

Still referring to FIG. 2, it can be seen that the tip portion 28 of the cryotip 24 is formed to surround an expansion chamber 56 that extends from the proximal end 34 substantially to the distal end 36 of the tip portion 28. The proximal end 34 of the tip portion 28 provides fluid access to the expansion chamber 56, and the distal end 36 of the tip portion 28 partially encloses the expansion chamber 56. Preferably, the tip portion 28 has a substantially cylindrical shape defining a longitudinal axis 58. As shown, the fluid lumen 48 of the reconfiguration segment 26 preferably extends into the expansion chamber 56. Importantly, the tip portion 28 of the cryotip 24 is made of a thermally conductive material and is in thermal communication with the reconfiguration segment 26.

Referring now to FIGS. 1 and 2, the straightening member 38 is dimensioned for insertion into the configuration lumen 22 of the catheter tube 12 and the configuration lumen 52 of the reconfiguration segment 26. Preferably, the straightening member 38 is a thin, elongated, stiff rod with a circular cross-section. Structurally, the straightening member 38 is more rigid than the reconfiguration segment 26 so that it shapes the reconfiguration segment 26 into a substantially straight configuration when the straightening member 38 is inserted into the configuration lumen 52 of the reconfiguration segment 26. Accordingly, the straightening member 38 structurally supports the reconfiguration segment 26 when the straightening member 38 is positioned in the configuration lumen 52. As will be appreciated by the skilled artisan, the straightening member 38 has the required flexibility that allows it to be advanced through, and positioned in, the vasculature of a patient. Furthermore, the straightening member 38 interacts with the configuration lumens 22 and 52 to allow the straightening member 38 to be inserted and withdrawn from the configuration lumens 22 and 52.

Figure 3:
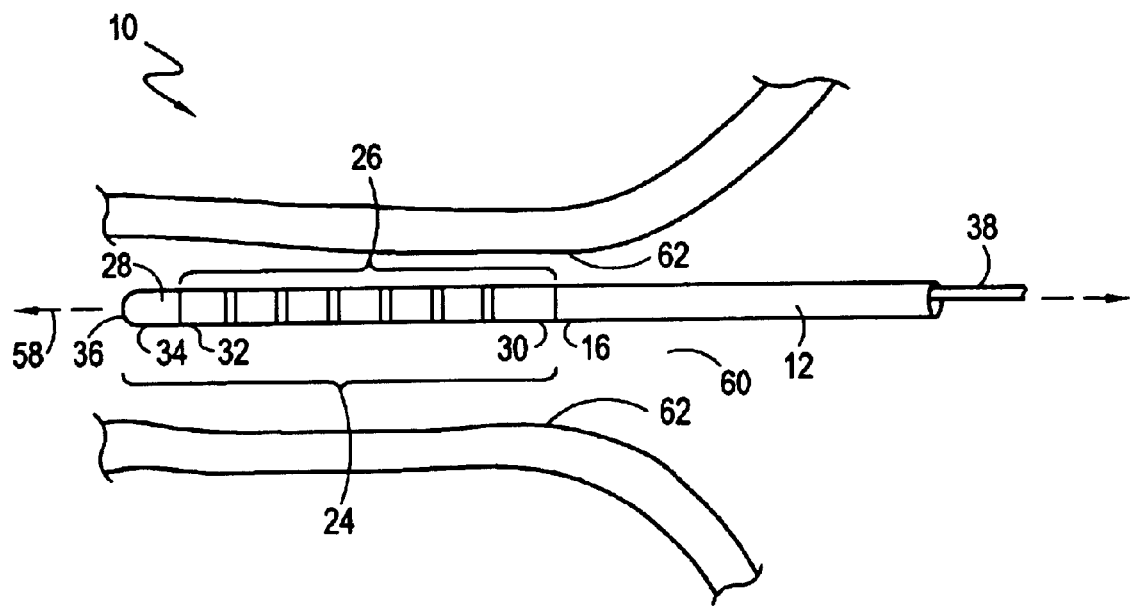
FIG. 3 is a perspective view of the cryoablation catheter in accordance with the present invention, shown in the straight configuration as positioned at the ostium of a pulmonary vein.

Operation of the system 10 can perhaps be best described with reference to FIGS. 3 and 4. Referring to FIG. 3, the cryotip 24 is advanced through the vasculature of a patient to a target site 60 with the straightening member 38 positioned in the configuration lumen 52 (FIG. 2) of the reconfiguration segment 26. As shown, the reconfiguration segment 26 is in the straight configuration. In the straight configuration, the straightening member 38 is preferably positioned substantially along the longitudinal axis 58 defined by the tip portion 28. At the target site 60, the cryotip 24 is positioned near the target tissue 62 to be cryoablated.

Figure 4:
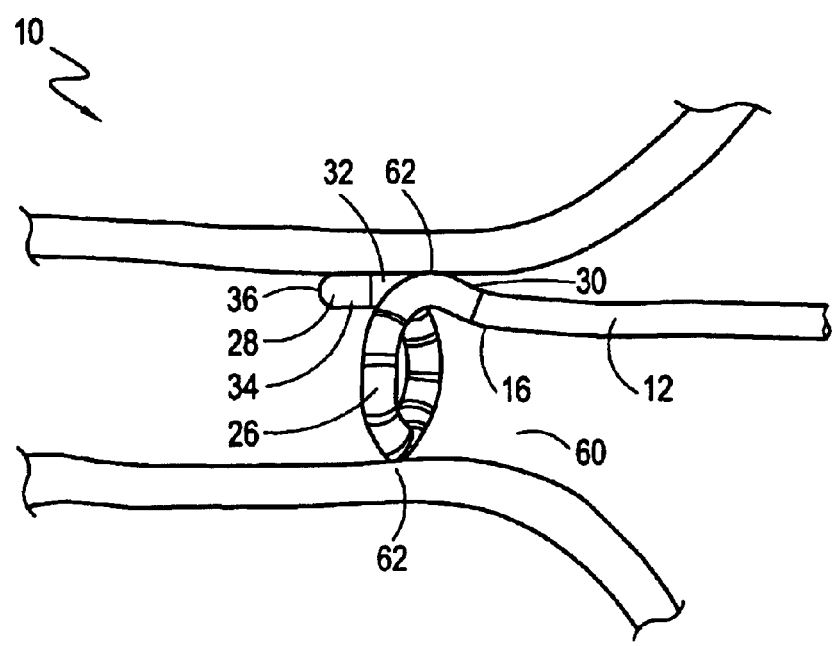
FIG. 4 is a perspective view of the cryoablation catheter in accordance with the present invention, shown in the spiral configuration with the cryotip contacting tissue around the ostium of a pulmonary vein.

Referring now to FIG. 4, at the target tissue 62, the straightening member 38 is withdrawn from the lumen 52 of the reconfiguration segment 26 to allow the reconfiguration segment 26 to assume its preformed shape. Preferably, the reconfiguration segment 26 has a preformed spiral shape and therefore assumes the spiral configuration when the straightening member 38 is withdrawn from the configuration lumen 52 of the reconfiguration segment 26. Accordingly, the reconfiguration segment 26 transforms from the straight configuration into the spiral configuration and is urged into contact with the target tissue 62. Preferably, the reconfiguration segment 26 is placed in contact with the target tissue 62 as it transforms into the spiral configuration.

With the cryotip 24 placed in contact with the target tissue 62, a refrigerant fluid is transferred from the fluid source 46 (FIG. 1) through the supply line 40 and the fluid lumens 18 and 48 into the expansion chamber 56 of the tip portion 28 (FIG. 2). Inside the expansion chamber 56, the fluid undergoes endothermic expansion to absorb heat from the tip portion 28 as the fluid is transformed into a gas inside the expansion chamber 56. In this process, the tip portion 28 is cooled. The gas is then removed from the expansion chamber 56 through the return lumens 20 and 50 to allow additional fluid to be introduced into the chamber 56. Importantly, the reconfiguration segment 26 is in thermal communication with the tip portion 28 and is therefore also cooled when the tip portion 28 is cooled. Accordingly, the target tissue 62 that is in contact with the reconfiguration segment 26 can be cryoablated.

After a procedure has been completed at the target site 60, the straightening member 38 can be reinserted into the configuration lumen 52 of the reconfiguration segment 26 to reconfigure the reconfiguration segment 26 into the straight configuration (See FIG. 3). The cryotip 24 can then be withdrawn from the target site 60 and removed from the vasculature of the patient.

While the particular cryoablation catheter system and method as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A catheter for cryoablating tissue which comprises:
    a catheter tube having a proximal end and a distal end;
    a straightening member;
    a cryotip formed with a fluid lumen, and a configuration lumen, and a tip portion, said cryotip being attached to and extending distally from said distal end of said catheter tube, with said cryotip being reconfigurable between a straight configuration when said straightening member is inserted into said configuration lumen and a spiral configuration when said straightening member is removed therefrom to reconfigure said cryotip in the spiral configuration and position said cryotip against tissue to be cryoablated, and wherein said tip portion is formed with an expansion chamber in fluid communication with said fluid lumen for receiving a refrigerant fluid and for allowing the refrigerant fluid to expand in said expansion chamber to cool said cryotip; and
    a means for introducing the refrigerant fluid through said fluid lumen of said cryotip to said tip portion to cool said cryotip for cryoablation of the tissue.

2. A catheter as recited in claim 1 wherein said cryotip is made of a thermally conductive polymer.

3. A catheter as recited in claim 2 wherein said polymer is heat set into the spiral configuration.

4. A catheter as recited in claim 1 wherein said straightening member is a stiff rod.

5. A catheter as recited in claim 1 wherein said cryotip is dimensioned to contact tissue around the periphery of the ostium of a pulmonary vein when said cryotip is in the spiral configuration.

6. A catheter as recited in claim 1 wherein said cryotip is further formed with a return lumen coupled in fluid communication with said expansion chamber for removing the refrigerant fluid from said expansion chamber.

7. A catheter as recited in claim 1 wherein the refrigerant fluid is nitrogen dioxide.

8. A catheter as recited in claim 1 wherein said means for introducing the refrigerant fluid through said fluid lumen is a fluid supply coupled in fluid communication with said fluid lumen.

9. A device for cryoablating tissue, said device comprising:

a cryotip having a proximal end and a distal end, and formed with a fluid lumen and a configuration lumen substantially therebetween, wherein said cryotip includes a tip portion formed with an expansion chamber in fluid communication with said fluid lumen, and said cryotip is reconfigurable between a spiral configuration and a straight configuration, with said cryotip biased to have the spiral configuration;

a means for configuring said cryotip into the straight configuration;

a means for positioning said cryotip in the straight configuration at the tissue to be cryoablated;

a means for contacting said cryotip in the spiral configuration against the tissue to be cryoablated; and a means for cooling said cryotip in the spiral configuration to wherein said means for cooling said cryotip includes a fluid supply coupled in fluid communication with said fluid lumen for introducing a refrigerant fluid through said fluid lumen into said expansion chamber to cool said cryotip to cryoablate the tissue.

10. A device as recited in claim 9 wherein said means for configuring said cryotip is a straightening member for insertion into said configuration lumen to configure said cryotip into the straight configuration.

11. A device as recited in claim 9 wherein said means for positioning said cryotip is a catheter tube attached to said proximal end of said cryotip for advancing said cryotip through the vasculature of a patient to position said cryotip at the tissue to be cryoablated.

12. A device as recited in claim 9 wherein said cryotip further comprises a reconfiguration segment formed with said fluid lumen and said configuration lumen, and a return lumen, with said return lumen coupled in fluid communication with said expansion chamber for removing the refrigerant fluid from said expansion chamber.

13. A device as recited in claim 12 wherein said reconfiguration segment is made of a thermally conductive polymer material and is heat set into the spiral configuration.

14. A method for cryoablating tissue, said method comprising the steps of:

providing a cryotip formed with a fluid lumen and a configuration lumen, and being reconfigurable between a spiral configuration and a straight configuration, with said cryotip biased to have the spiral configuration, and wherein said cryotip includes a tip portion formed with an expansion chamber;

configuring said cryotip into the straight configuration;

positioning said cryotip in the straight configuration at the tissue to be cryoablated;

reconfiguring said cryotip into the spiral configuration to contact said cryotip against the tissue to be cryoablated; and introducing a refrigerant fluid through said fluid lumen and into said expansion chamber for expansion therein to cool said cryotip to cryoablate the tissue.

15. A method as recited in claim 14 wherein said cryotip is formed with a return lumen in fluid communication with said expansion chamber, said method further comprising the step of removing the refrigerant fluid from said expansion chamber through said return lumen.

16. A method as recited in claim 14 wherein said step of configuring said cryotip into the straight configuration further comprises the step of inserting a straightening member into said configuration lumen of said cryotip, and wherein said step of reconfiguring said cryotip into the spiral configuration further comprises the step of removing said straightening member from said configuration lumen of said cryotip to allow said cryotip to assume the spiral configuration.

17. A method as recited in claim 14 wherein said cryotip is dimensioned to contact tissue around the periphery of the ostium of a pulmonary vein when said cryotip is in the spiral configuration.

* * * * *